US00PP31019P2

(12) United States Plant Patent
Klemm et al.

(10) Patent No.: US PP31,019 P2
(45) Date of Patent: Nov. 5, 2019

(54) ***DIANTHUS* PLANT NAMED 'KLEDG18305'**

(50) Latin Name: ***Dianthus* sp.**
Varietal Denomination: KLEDG18305

(71) Applicant: Klemm+Sohn GmbH & Co. KG, Stuttgart (DE)

(72) Inventors: Nils Klemm, Stuttgart (DE); Lena Gutbrodt, Bempflingen (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 15/998,600

(22) Filed: Aug. 16, 2018

(51) Int. Cl.
*A01H 5/02* (2018.01)
*A01H 6/30* (2018.01)

(52) U.S. Cl.
USPC ..... Plt./276
CPC ..... *A01H 6/305* (2018.05)

(58) Field of Classification Search
USPC ..... Plt./276
CPC ..... A01H 6/305; A01H 5/02
See application file for complete search history.

*Primary Examiner* — Keith O. Robinson
(74) *Attorney, Agent, or Firm* — Bethany R. Roahrig; Cochran Freund & Young LLC

(57) ABSTRACT

A new *Dianthus* plant particularly distinguished by salmon-pink flowers with a red ring, and an upright habit, is disclosed.

1 Drawing Sheet

Genus and species: *Dianthus* sp.
Variety denomination: 'KLEDG18305'.

CROSS REFERENCE TO RELATED APPLICATION

A Canadian Plant Breeders Rights Application for this variety was filed on Apr. 27, 2018, Application No. 18-9432, and a European Community Plant Variety Protection Application for this variety was filed on Apr. 24, 2018, Application No. 2018/1131. 'KLEDG18305' has not been sold or made publicly available more than one year prior to the filing date of the present application.

BACKGROUND OF THE NEW PLANT

The present invention comprises a new and distinct variety of *Dianthus*, botanically known as *Dianthus* sp., and hereinafter referred to by the variety name 'KLEDG18305'. 'KLEDG18305' originated from an open pollination of the proprietary female parent 'DSU-2013-0017' (unpatented) and an unknown male *Dianthus* variety in July 2014, in Stuttgart, Germany. A single plant was selected in July 2015 and designated 'KLEDG18305'.

In September 2015, 'KLEDG18305' was first vegetatively propagated by vegetative cuttings in Stuttgart Germany. 'KLEDG18305' was found to reproduce true to type in successive generations of asexual propagation in Latina, Italy via vegetative stem cuttings.

SUMMARY

The following are the most outstanding and distinguishing characteristics of this new variety when grown under normal horticultural practices in Stuttgart, Germany.

1. Salmon-pink flowers with a red ring; and
2. An upright habit.

DESCRIPTION OF THE PHOTOGRAPH

This new *Dianthus* plant is illustrated by the accompanying photograph of a plant approximately 11 weeks old and grown in a greenhouse in Stuttgart, Germany. The photograph shows the whole plant, including the flowers and foliage and buds and was taken in January 2018 in Stuttgart, Germany. The colors shown are as true as can be reasonably obtained by conventional photographic procedures.

DESCRIPTION OF THE NEW VARIETY

The following detailed descriptions set forth the distinctive characteristics of 'KLEDG18305'. The data which define these characteristics were collected from asexual reproductions carried out in Stuttgart, Germany. Data was collected in April 2018 on 6-month old plants grown in a plastic greenhouse. Color references are to The R.H.S. Colour Chart of The Royal Horticultural Society of London (R.H.S.), 5$^{th}$ edition (2007).

Classification:
- *Family*.—Caryophyllaceae.
- *Botanical*.—*Dianthus* sp.
- *Common*.—Pot carnation.
- *Designation*.—'KLEDG18305'.

Parentage:
- *Female parent*.—The proprietary *Dianthus* variety 'DSU-2013-0017' (unpatented).
- *Male parent*.—An unknown proprietary *Dianthus* variety.

Plant:
- *Plant form*.—Upright.
- *Plant height*.—13.0 cm to 15.0 cm.
- *Plant diameter or spread*.—16.0 cm to 18.0 cm.
- *Propagation type*.—Vegetative cuttings, stem cutting.
- *Time to produce a rooted young plant*.—10 to 14 days.
- *Root description*.—White, fine. Young roots: RHS161D. Mature roots: RHS199C.
- *Rooting habit (shape)*.—Lanceolate.

Lateral branches:
- *Number of lateral branches*.—4 to 6.
- *Flower clustering on the lateral branch*.—In all lateral branches.

*Strength*.—Moderate.
*Length*.—10.0 cm to 12.0 cm.
*Diameter*.—0.3 cm to 0.4 cm.
*Internode length*.—2.0 cm to 2.5 cm.
*Number of internodes per branch/stem*.—5.
*Node length*.—0.3 cm to 0.4 cm.
*Node diameter*.—0.3 cm.
*Texture*.—Smooth.
*Color*.—RHS N137A.
*Branch/stem appearance*.—Solid.

Foliage:
*Arrangement*.—Opposite.
*Length*.—4.0 cm to 6.0 cm.
*Width*.—0.4 cm to 0.6 cm.
*Shape*.—Lanceolate.
*Apex*.—Acute.
*Base*.—Obtuse.
*Margin*.—Entire.
*Curvature of the leaf*.—Weakly recurved.
*Texture (both upper and lower surfaces)*.—Smooth.
*Immature leaf color*.—Upper surface: RHS 143A. Lower surface: RHS 143B.
*Mature leaf color*.—Upper surface: RHS N137B. Lower surface: RHS 137B.
*Venation pattern*.—Parallel.
*Venation color*.—Upper surface: RHS N137B. Lower surface: RHS 137B.

Flowers:
*Flower type and habit*.—Single flower, small sprays.
*Diameter of the flower*.—2.3 cm to 2.8 cm.
*Fragrance*.—Present, typical of a carnation.
*Natural flowering season*.—Spring to fall.
*Position of flowers relative to the foliage*.—Moderately above.
*Number of flowers per spray*.—3 to 4.
*Flower longevity on the plant*.—14 to 17 days.
*Buds*.—Length: 1.5 cm to 2.0 cm. Diameter: 0.3 cm to 0.5 cm. Shape: Elliptic. Color: RHS 138A. Extrusion of the styles at the bud stage: Absent.
*Corolla*.—Quantity of petals and arrangement: 5. Corolla height: 0.2 cm to 0.4 cm. Corolla diameter: 2.2 cm to 2.7 cm. Arrangement of the corolla: Petals are overlapping lightly, round shape, slightly undulate profile. Petal length: 2.5 cm to 2.8 cm. Petal width: 1.0 cm to 1.5 cm. Petal shape: Spoon-shaped. Petal apex: Obtuse. Petal base: Acute. Petal margin: Crenate. Depth of petal margin: Shallow. Petal texture (both upper and lower surfaces): Smooth. Petal luster (both surfaces): Dull. Petal color: Immature: Upper surface: RHS 50B; in summer with red ring RHS 42A. Lower surface: RHS 48D. Mature: Upper surface: RHS 49A; in summer with red ring RHS 42A. Lower surface: RHS 51D. Macule size of petal: Medium.
*Calyx*.—Quantity of sepals and arrangement: Composed of 5 sepals, fused. Shape: Campanulate. Calyx height: 1.0 cm to 1.5 cm. Calyx diameter (at the apex): 0.4 cm to 0.5 cm. Longitudinal axis of lobes: Straight. Sepal texture (both upper and lower surfaces): Smooth. Sepal color: Upper surface: RHS 137A. Lower surface: RHS 137D. Sepal length: 0.7 cm to 0.9 cm. Sepal diameter: 0.3 cm to 0.4 cm. Sepal apex: Acute. Sepal base: Obtuse. Sepal margin: Entire. Sepal luster (both surfaces): Dull. Sepal arrangement: Fused.

Peduncles:
*Length*.—1.0 cm to 1.5 cm (last internode).
*Diameter*.—0.1 cm to 0.15 cm.
*Strength*.—Moderate.
*Texture*.—Smooth.
*Color*.—RHS 137A.

Reproductive organs:
*Stamens*.—Quantity per flower: 3 to 5 rudimentary, reduced. Filament length: 0.2 cm to 0.5 cm. Filament color: RHS 155B. Anther length: 0.05 cm. Anther diameter: Less than 0.05 cm. Anther color: RHS 161D. Pollen amount: Abundant. Pollen color: RHS 15A.
*Pistils*.—Quantity per flower: 1. Pistil length: 2.0 cm. Style length: 1.5 cm to 1.7 cm. Style color: RHS NN155B. Quantity of styles and shoulder of styles: 2 styles without shoulder are present. Stigma shape: Filamentous. Stigma color: RHS 53C. Ovary size: 0.5 cm to 0.7 cm. Ovary shape: Oval. Ovary surface: Slightly ribbed. Ovary color: RHS 145A.

Fruit and seed set: Seed is sometimes observed, but no information on the seed is available.

Disease and pest/insect resistance: No disease and pest/insect resistance observed.

COMPARISON WITH PARENTAL LINE AND KNOWN VARIETY

'KLEDG18305' is distinguished from its female parent as described in Table 1.

TABLE 1

Comparison with Parental Lines

| Characteristic | 'KLEDG18305' | Female Parent 'DSU-2013-0017' |
|---|---|---|
| Flower color | Salmon-pink with a red ring | Pink, with a dark red ring |

'KLEDG18305' can be compared to the commercial *Dianthus* variety 'Pink Kisses', also known as 'KLEDG12163' (U.S. Plant Pat. No. 24,707). Differences between the varieties are described in Table 2.

TABLE 2

Comparison with Similar Variety

| Characteristic | 'KLEDG18305' | 'Pink Kisses' |
|---|---|---|
| Flower color | Salmon-pink with a red ring | Pink with a purple eye |

We claim:

1. A new and distinct variety of *Dianthus* plant designated 'KLEDG18305' as illustrated and described herein.

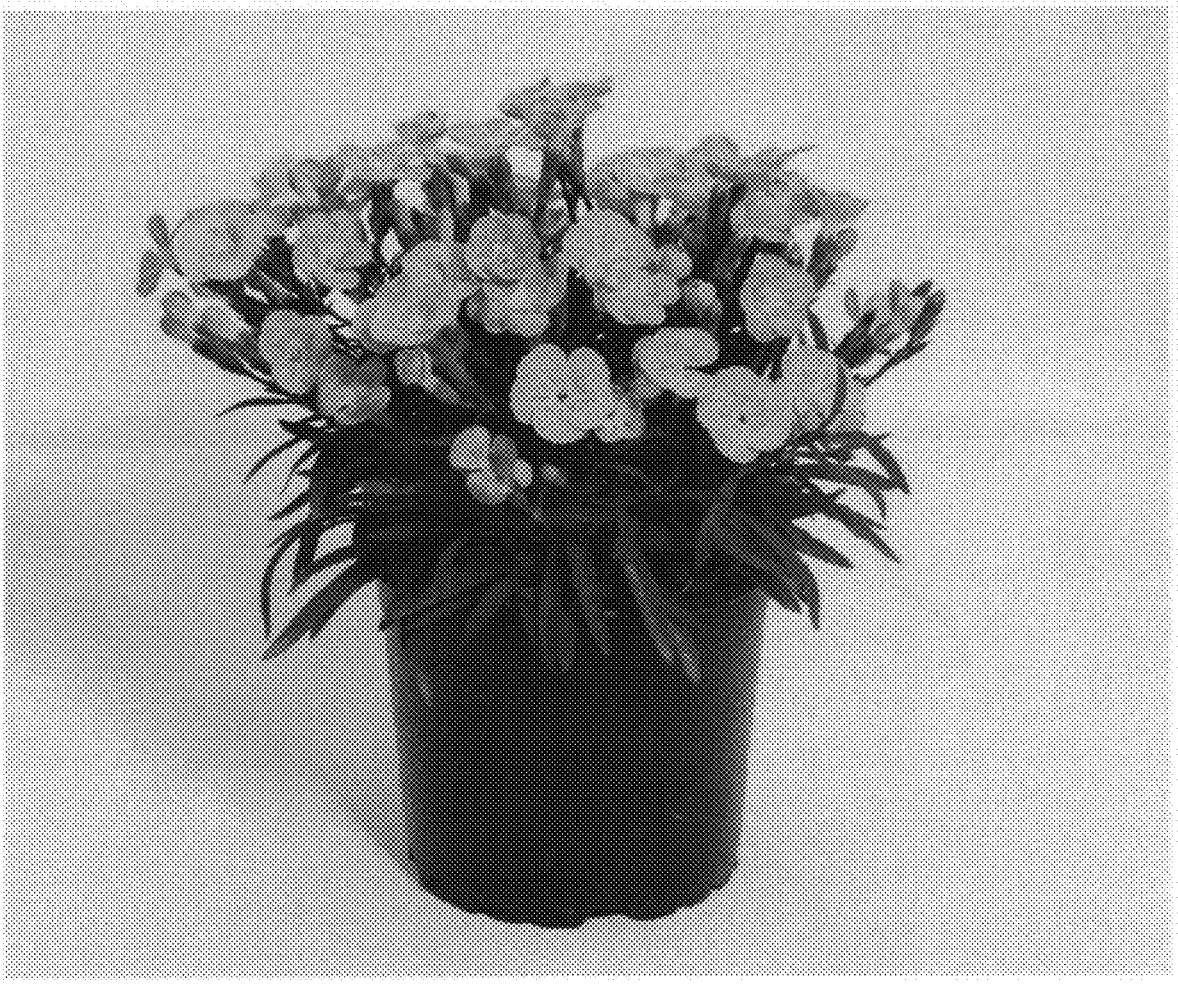

* * * * *